United States Patent
Cannata et al.

[11] Patent Number: 5,856,482
[45] Date of Patent: Jan. 5, 1999

[54] PROCESS FOR THE PRODUCTION OF THE FORM I OF THE TERAZOSIN MONOHYDROCHLORIDE ANHYDROUS

[75] Inventors: Vincenzo Cannata, Bologna; Tiziano Ferrario; Barbara Galbiati, both of Milan, all of Italy

[73] Assignee: ALFA Chemicals Italiana S.R.L., Bergamo, Israel

[21] Appl. No.: 957,976

[22] Filed: Oct. 21, 1997

[30] Foreign Application Priority Data

Nov. 29, 1996 [IT] Italy ................. BO96A0612

[51] Int. Cl.⁶ ................................................. C07D 405/14
[52] U.S. Cl. ................................. 544/291; 514/260
[58] Field of Search ................................. 544/291

[56] References Cited

U.S. PATENT DOCUMENTS

| | | | |
|---|---|---|---|
| 4,026,894 | 5/1977 | Winn et al. | 544/291 |
| 4,251,532 | 2/1981 | Roteman | 544/291 |
| 5,294,615 | 3/1994 | Meyer et al. | 544/291 |
| 5,362,730 | 11/1994 | Baver et al. | 544/291 |
| 5,412,095 | 5/1995 | Morley et al. | 544/291 |
| 5,587,377 | 12/1996 | Patel et al. | 544/291 |
| 5,675,006 | 10/1997 | Karimian et al. | 544/283 |
| 5,686,612 | 11/1997 | Karimian et al. | 544/284 |

FOREIGN PATENT DOCUMENTS 9721705  6/1997  WIPO .

*Primary Examiner*—Emily Bernhardt
*Attorney, Agent, or Firm*—Bucknam And Archer

[57] ABSTRACT

The process for the production of the form I of the terazosin monohydrochloride anhydrous consists of treating at the boiling temperature terazosin monohydrochloride dihydrate with a mixture of methanol and a solvent selected from $C_2$–$C_6$ straight or branched alcohols, the esters of the C–$C_8$ carboxylic aliphatic acids with $C_1$–$C_8$ straight or branched alcohols, $C_3$ to $C_8$ aliphatic ketones, $C_4$ to $C_8$ straight, branched or cyclic aliphatic ethers, aliphatic amides and the aliphatic nitriles.

2 Claims, 3 Drawing Sheets

PROCESS FOR THE PRODUCTION OF THE FORM I OF THE TERAZOSIN MONOHYDROCHLORIDE ANHYDROUS

BACKGROUND OF THE INVENTION

The compound 1-(4-amino-6,7-dimethoxy-2-quinazolinyl)-4-(tetrahydro-2-furoyl)piperazine is internationally known under the name of terazosin.

This compound, together with the anhydrous monohydrochloride salt, has been described for the first time in U.S. Pat. No. 4,026,894.

In the subsequent U.S. Pat. No. 4,251,532 a crystalline dihydrate form of terazosin has been described defined more stable than the original anhydrous form. This dihydrate form of the terazosin monohydrochloride is at present marketed all over the world, for instance as HYTRIN® in USA and United Kingdom and as ITRIN® in Italy, for the treatment of the hypertension.

Recently U.S. Pat. No. 5,412,095 has described and claimed new crystalline forms of the terazosin monohydrochloride anhydrous, named FORM II and FORM III, and a new process for producing the original anhydrous monohydrochloride crystalline form described in U.S. Pat. No. 4,026,894 named "a posteriori" FORM I.

SUMMARY OF THE INVENTION

Object of the present invention is a process for the production of the 1-(4-amino-6,7dimethoxy-2-quinazolinyl)-4-(tetrahydro-2-furoyl) piperazine monohydrochloride anhydrous in the crystalline form I described in U.S. Pat. Nos. 4,026,894 and 5,412,095.

The 1-(4-amino-6,7-dimethoxy-2-quinazolinyl)-4-(tetrahydro-2-furoyl)piperazine mono-hydrochloride anhydrous is quickly added under strong stirring to a mixture heated to the boiling temperature made of methanol and a solvent selected from $C_2$–$C_6$ straight or branched alcohols, the esters of $C_1$–$C_8$ carboxylic aliphatic acids $C_1$–$C_8$ straight or branched alcohols, the aliphatic $C_3$–$C_8$ ketones; straight or branched or cyclic aliphatic ethers, from $C_4$ to $C_8$, aliphatic amides and the aliphatic nitriles.

In a preferred aspect of the invention the solvent is selected from ethanol, isopropanol, n-butanol, n-butyl acetate, acetone, methylisobutylketone and n-dibutylether and the mixture is made an amount by volume of methanol between 1 and 8 times and an amount by volume of a solvent between 3 and 15 times the weight of the 1-(4-amino-6,7-dimethoxy-2-quinazolinyl)-4-tetrahydro-2-furoyl) piperazine monohydrochloride dihydrate.

At the end of the addition the reaction mixture is kept at the boiling temperature under strong stirring for a period of time between 30 minutes and 3 hours and the mixture of methanol/solvent is partially distilled off.

The suspension is then cooled to 20° C. under nitrogen atmosphere and filtered. The crystalline solid is washed with the solvent and dried in oven under vacuum at a temperature between 70° C. and 75° C. for a period of time between 12 and 24 hours.

The so obtained pure product has been characterized through three kinds of structural analytic techniques: powder X-ray diffraction, IR spectrum and differential thermal analysis.

The technique of powder X-ray diffraction has been carried out by means of an automatic powder diffractometer Philips model PW1050, controlled by a PW1710 unit, with Bragg-Brentano geometry, by means of monochromatic CuK$_\alpha$ radiation (wavelength 1.54060 Å, 40 kV and 40 mA) with scansion interval 3–40 in 2θ in degrees, angular pitch 0.02 degrees and scansion time 1.25 seconds for angular pitch and at room temperature.

The samples have been prepared dry by light grinding in agate mortar without compression.

BRIEF DESCRIPTION OF THE DRAWINGS

The intensities of the diffracted X rays (counts) in function of the diffraction angle 2Θ are reported in the diffractogram of FIG. 1.

The IR spectrum, reported in FIG. 2, has been carried out by means of a FT-IR Perkin Elmer 6100 spectrophotometer on samples containing 0.3% of product in KBr with registration between 4400 and 600 cm$^{-1}$.

Figure 3:
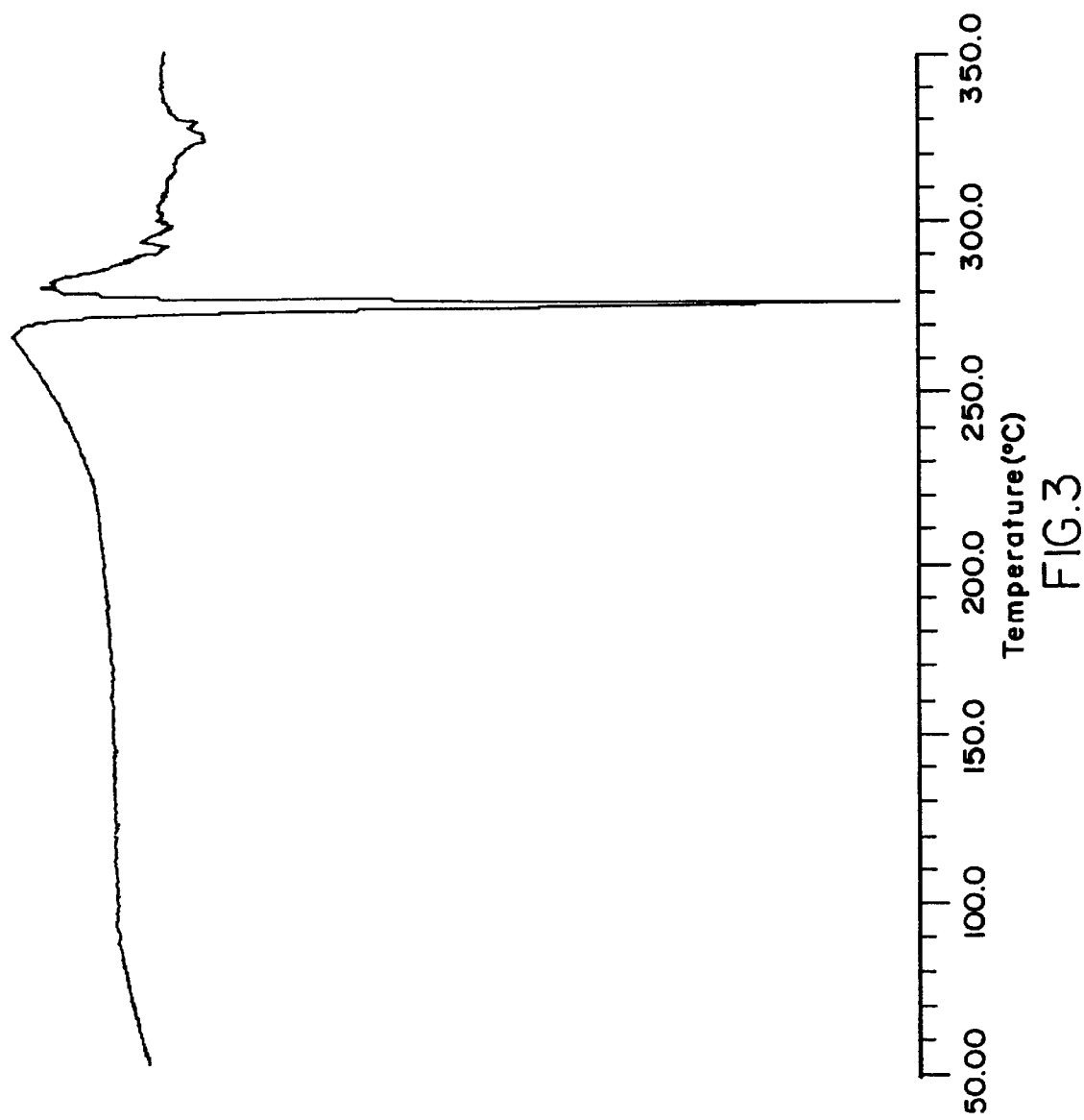

The differential thermal analysis, with the thermogram reported in FIG. 3, has been carried out with an instrument DSC METTLER TA 4000, starting from an initial temperature of 50° C. till a temperature of 350° C. and with a scansion speed equal to 5° C./nmin. The analysis has been carried out on a holed melting-pot containing an amount of substance between 4 and 6 mgs.

DESCRIPTION OF THE INVENTION

This process is much more advantageous than that described in U.S. Pat. No. 5,412,095 as it is carried out in a very simple way as regards the operative conditions and with equipments normally used in the industrial synthesis plants, in a single step with very high yields, greater than 90%.

On the contrary, the process described in the above mentioned U.S. Patent processed, under strictly anhydrous conditions, through the formation and the isolation of a methanolate hydrochloride intermediate, with yields of about 93%, followed by the subsequent transformation of the methanolate hydrochloride into anhydrous hydrochloride, with yields of about 78%, so that the overall final yield is about 72%.

Therefore the new process is remarkably better than that described in U.S. Pat. No. 5,412,095, both from the manufacture and the cost point of view.

The examples hereinbelow reported have to be considered as a further illustration of the invention and not as an its limitation.

EXAMPLE 1

10 Grams of 1-(4-amino-6,7-dimethoxy-2-quinazolinyl)-4-(tetrahydro-2-furoyl) piperazine monohydrochloride dihydrate are quickly added under strong stirring to a boiling mixture made of 50 ml of methanol and 75 ml of n-butyl acetate in a three-necked flask equipped with stirrer and cooling coil. About 50 ml of the solvent mixture are distilled off after one hour of heating to the boiling temperature under stirring, then the suspension is cooled to 20° C. and filtered.

The obtained product is washed with 10 ml of n-butyl acetate and dried in an oven under vacuum at 70° C. for 12 hours obtaining 8.8 g of product with a yield equal to 95.7%.

Figure 1:
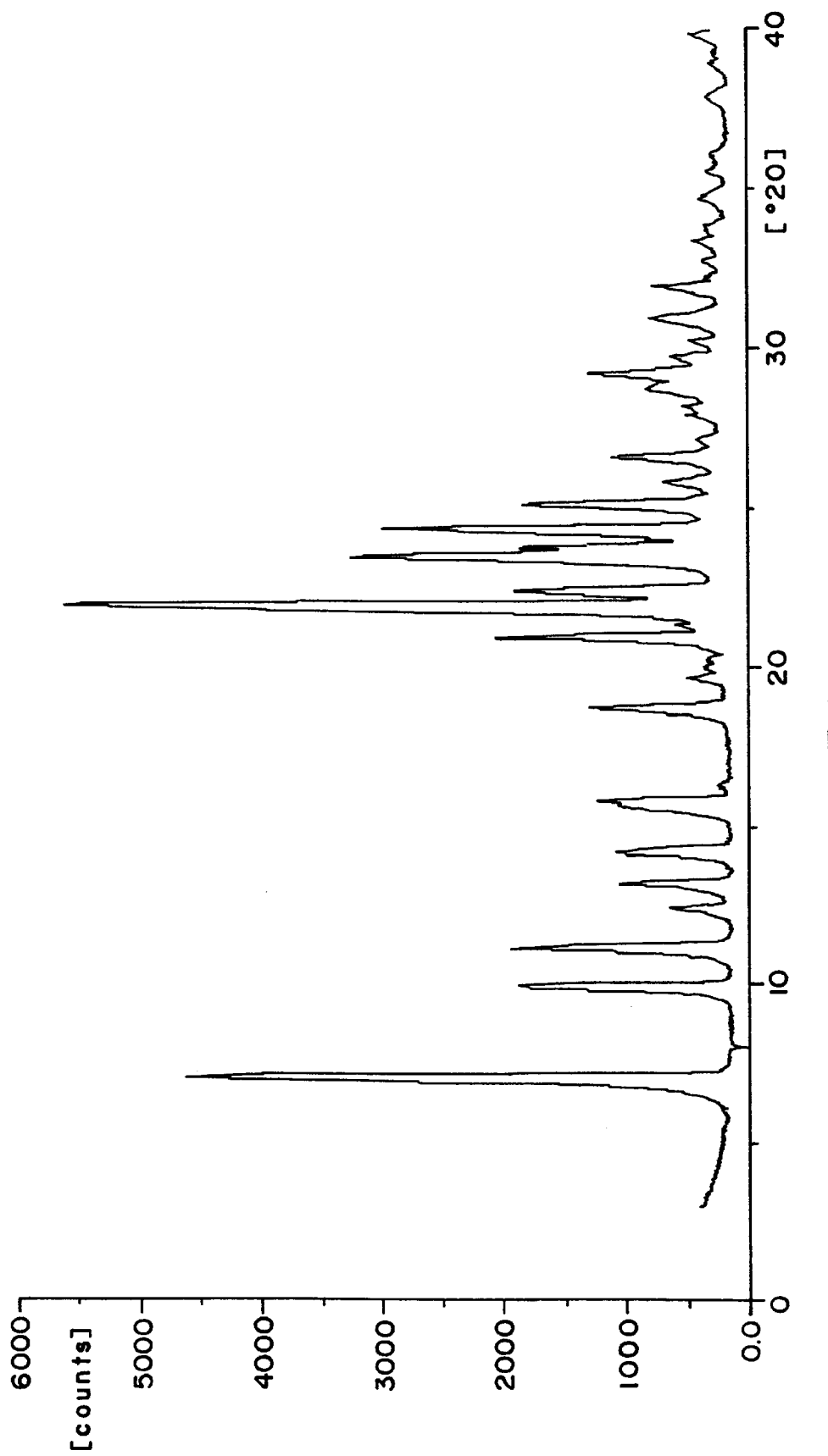
Figure 2:
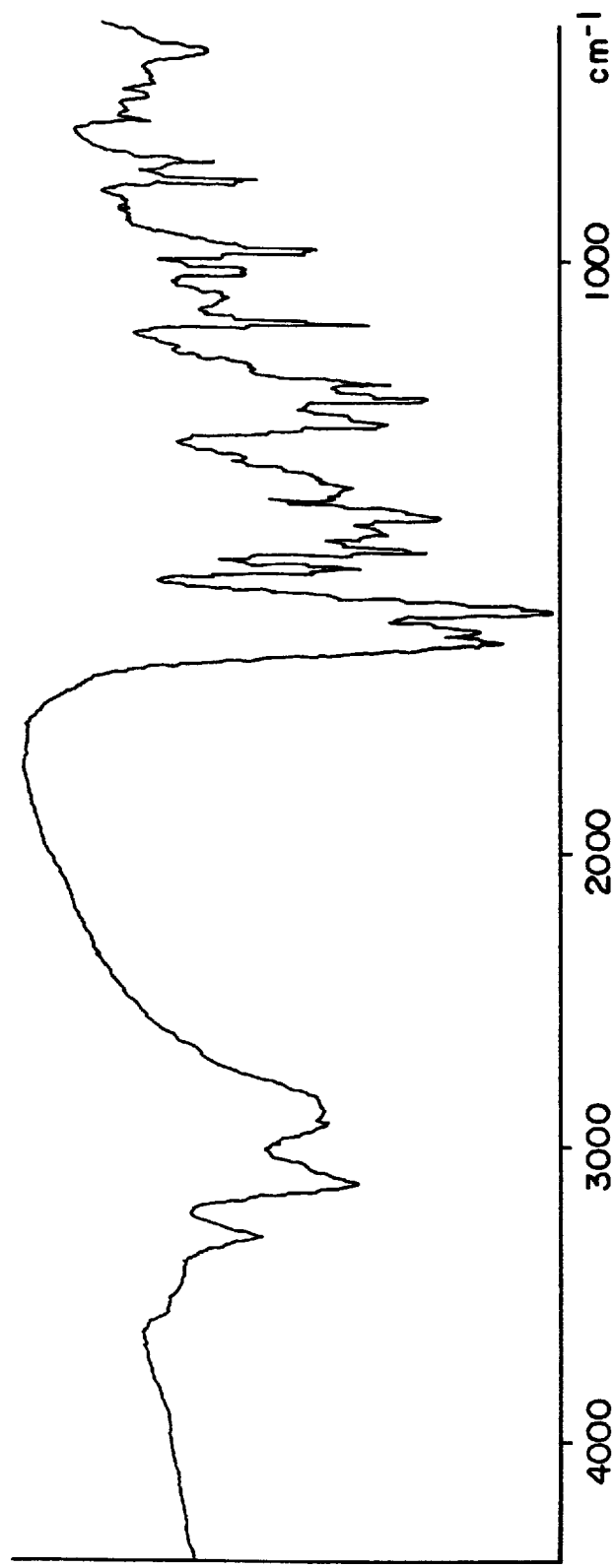

Samples of the product have been submitted to three kinds of structural analytical techniques: powder X-ray diffraction (FIG. 1), IR spectrum (FIG. 2) and differential thermal analysis (FIG. 3). The diffraction angles 2θ more significant, with an approximation of ±0.2°, obtained in the powder X-ray diffraction are as follows: 7.15°, 10.04°; 11.08°; 11.22°; 14.20°; 15.90°; 18.78°; 20.91°; 21.90°; 22.42°; 23.45°; 23.75°; 24.35°; 25.10° and 29.15°.

EXAMPLE 2

Example 1 is repeated by using n-butanol instead of n-butyl acetate and obtaining 8.6 g of product, having the same chemical-physical characteristics as those of the product of example 1, with a yield equal to 92.6%.

EXAMPLE 3

Example 1 is repeated by using isobutylmethylketone instead of n-butyl acetate and obtaining 9.1 g of product, having the same chemical-physical characteristics as those of the product of example 1, with a yield equal to 98.0%.

EXAMPLE 4

Example 1 is repeated by using acetone instead of n-butyl acetate and obtaining 8.3 g of product, having the same chemical-physical characteristics as those of the product of example 1, with a yield equal to 89.4%.

EXAMPLE 5

Example 1 is repeated by using ethanol instead of n-butyl acetate and obtaining 8.1 g of product, having the same chemical-physical characteristics as those of the product of example 1, with a yield equal to 87.6%.

EXAMPLE 6

Example 1 is repeated by using isopropanol instead of n-butyl acetate and obtaining 8.8 g of product, having the same chemical-physical characteristics as those of the product of example 1, with a yield equal to 94.5%.

We claim:

1. A process for the preparation of the anhydrous crystalline form I of 1-(4-amino-6,7-dimethoxy-2quinazolinyl)-4-(tetrahydro-2-furoyl)piperazine monohydrochloride which comprises the steps of:

a) quickly adding under strong stirring (4-amino-6,7-dimethoxy-2-quinazolinyl)-4-(tetrahydro-2-furoyl) piperazine monohydrochloride dihydrate to a boiling mixture of methanol and a solvent which is a member selected from the group consisting of straight or branched $C_2$ to $C_6$ alcohols, esters of $C_1$–$C_8$ aliphatic carboxylic acids with straight or branched $C_1$ to $C_8$ alcohols, $C_3$ to $C_8$ aliphatic ketones, $C_4$ to $C_8$ straight, branched or cyclic aliphatic ethers, aliphatic amides and aliphatic nitriles;

b) heating to the boiling temperature under strong stirring for a period of time between 30 minutes and 3 hours;

c) partially distilling off said mixture of methanol and said solvent;

d) cooling subsequently the suspension to 20° C. and filtering to separate the solid;

e) washing the solid with the solvent and drying in an oven under vacuum at a temperature between 70° C. and 75° C. for a period of time between 12 and 24 hours.

2. The process according to claim 1 wherein said solvent is selected from the group consisting of ethanol, isopropanol, n-butanol, n-butyl acetate, acetone, methylisobutylketone and n-dibutylether and the mixture is made by an amount by volume of methanol between 1 and 8 times and by an amount by volume of said solvent between 3 and 15 times with respect of the weight of the 1-(4-amino-6,7-dimethoxy-2-quinazolinyl)-4-(tetrahydro-2-furoyl) piperazine monohydrochloride dihydrate.

* * * * *

UNITED STATES PATENT AND TRADEMARK OFFICE
CERTIFICATE OF CORRECTION

PATENT NO. : 5,856,482
DATED : January 5 1999
INVENTOR(S) : Vicenzo Cannata, et al It is certified that error appears in the above-identified patent and that said Letters Patent is hereby corrected as shown below:

On the title page,

[73]   Assignee: ALFA Chemicals Italiana S.R.L.
                              Bergamo, Italy Signed and Sealed this Twentieth Day of July, 1999

Attest:

Q. TODD DICKINSON

*Attesting Officer*                Acting Commissioner of Patents and Trademarks